United States Patent
Chen et al.

(10) Patent No.: US 9,157,062 B2
(45) Date of Patent: *Oct. 13, 2015

(54) COMPOSITIONS AND METHODS FOR PROMOTING THE GENERATION OF PDX1+ PANCREATIC CELLS

(71) Applicants: President and Fellows of Harvard College, Cambridge, MA (US); The General Hospital Corporation, Boston, MA (US)

(72) Inventors: Shuibing C. Chen, Arlington, MA (US); Douglas A. Melton, Lexington, MA (US); Malgorzata Borowiak, Somerville, MA (US); Julia Lamenzo Fox, Arlington, MA (US); Stuart L. Schreiber, Boston, MA (US); Lee F. Peng, Somerville, MA (US); Lance Davidow, Lexington, MA (US); Kelvin Lam, Arlington, MA (US); Lee L Rubin, Wellesley, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 18 days.

This patent is subject to a terminal disclaimer.

(21) Appl. No.: 14/282,647

(22) Filed: May 20, 2014

(65) Prior Publication Data

US 2014/0335611 A1 Nov. 13, 2014

Related U.S. Application Data

(63) Continuation of application No. 12/989,284, filed as application No. PCT/US2009/041381 on Apr. 22, 2009, now Pat. No. 8,728,812.

(60) Provisional application No. 61/047,056, filed on Apr. 22, 2008.

(51) Int. Cl.
| | |
|---|---|
| *C12N 5/07* | (2010.01) |
| *C12N 5/00* | (2006.01) |
| *C12N 5/0735* | (2010.01) |
| *C12N 5/071* | (2010.01) |

(52) U.S. Cl.
CPC ............ *C12N 5/0606* (2013.01); *C12N 5/0676* (2013.01); *C12N 2501/115* (2013.01); *C12N 2501/119* (2013.01); *C12N 2501/16* (2013.01); *C12N 2501/385* (2013.01); *C12N 2501/415* (2013.01); *C12N 2501/42* (2013.01); *C12N 2501/727* (2013.01); *C12N 2501/998* (2013.01); *C12N 2501/999* (2013.01); *C12N 2506/02* (2013.01)

(58) Field of Classification Search
CPC ......................... C12N 2506/02; C12N 2506/22
USPC .................................................. 435/366, 377
See application file for complete search history.

(56) References Cited

U.S. PATENT DOCUMENTS

| | | |
|---|---|---|
| 5,089,517 A | 2/1992 | Choi et al. |
| 8,728,812 B2 * | 5/2014 | Chen et al. ................... 435/377 |
| 2004/0121460 A1 | 6/2004 | Lumelsky et al. |
| 2004/0259244 A1 | 12/2004 | Scharp et al. |
| 2007/0259423 A1 | 11/2007 | Odorico et al. |

OTHER PUBLICATIONS

Chen, et. al., "A small molecule that directs differentiation of human ESCs into the pancreatic lineage," Nature Chem, 2009(5); 258-265.
Jiang, et al., Cell research, 2007(17); 333-344.
D'Amour et al., Nature Biotechnology, 2006(24); 1392-1401.
International Search Report for PCT/US2009/041381 dated Jan. 29, 2010.
Notice of Allowance for U.S. Appl. No. 12/989,284, dated Dec. 26, 2013.
Non-Final Office Action for U.S. Appl. No. 12/989,284, dated May 31, 2012.
Final Office Action for U.S. Appl. No. 12/989,284, dated Apr. 22, 2013.

* cited by examiner

*Primary Examiner* — Anoop Singh
*Assistant Examiner* — David A Montanari
(74) *Attorney, Agent, or Firm* — Lisa M. Warren, Esq.; Morse, Barnes-Brown & Pendleton, P.C.

(57) ABSTRACT

Certain embodiments disclosed herein are directed to a method of producing pancreatic cells or pancreatic cell precursors by exposing human embryonic stem cells to an effective amount of at least one compound listed in Table I to differentiate the human embryonic stem cells into the pancreatic cells or the pancreatic cell precursors. Kits and pancreatic cell lines produced using the methods are also described.

4 Claims, 13 Drawing Sheets

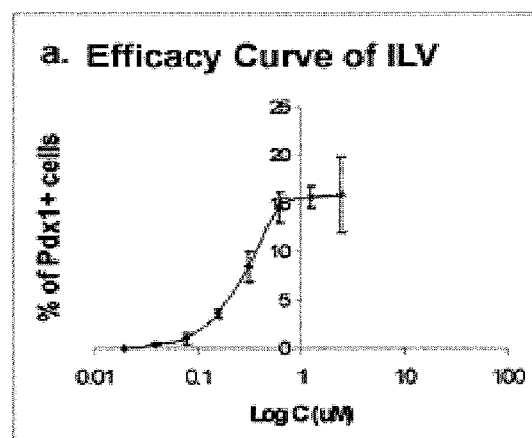
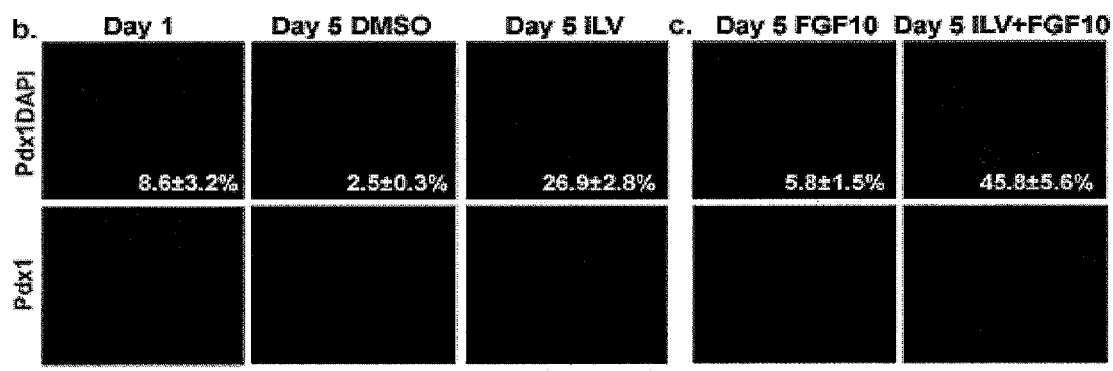
FIG. 2

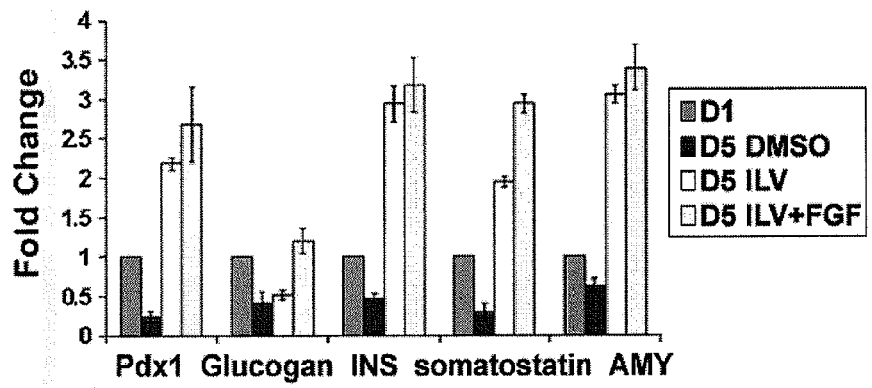
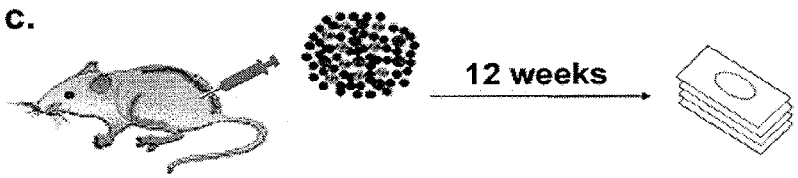
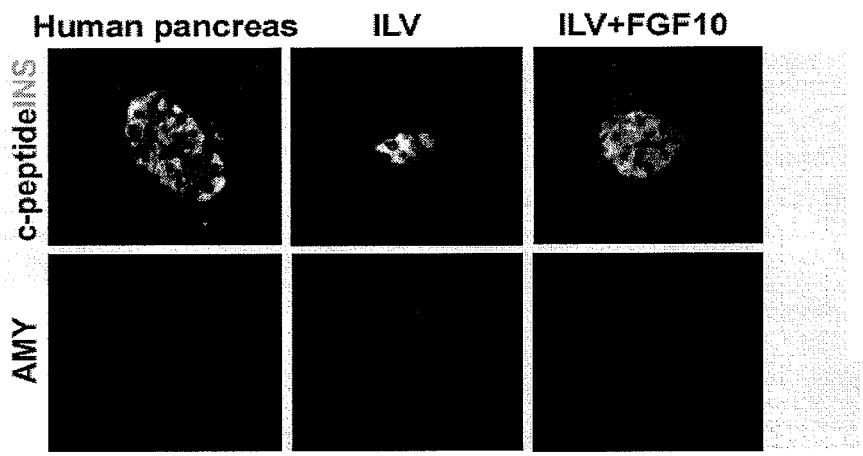
FIG. 5 (cont.)

Table I

| Compound | Compound Number | Commercial Source |
|---|---|---|
| (-)-Indolactam V | I | Axxora |
| Boldine | II | Sigma |
| Rotenone | III | Sigma |
| Ethopropazine hydrochloride | IV | Microsource |
| cedrelone | V | Microsource |
| prieurianin | VI | Microsource |
| strophanthidin | VII | Prestwick Chemical |
| trimeprazine tartrate | VIII | Prestwick Chemical |
| terconazole | IX | Prestwick Chemical |
| dimethisoquin hydrochloride | X | Prestwick Chemical |
| harmine hydrochloride | XI | Prestwick Chemical |

FIG. 9

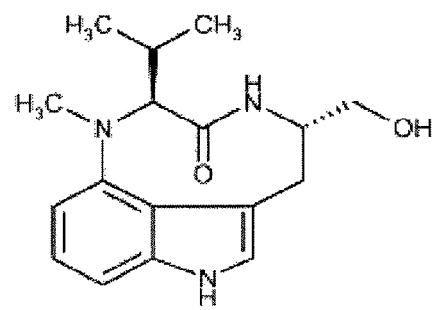
(-)-Indolactam V
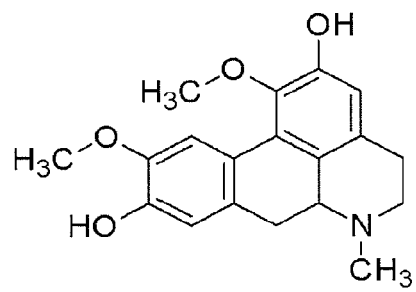
Boldine
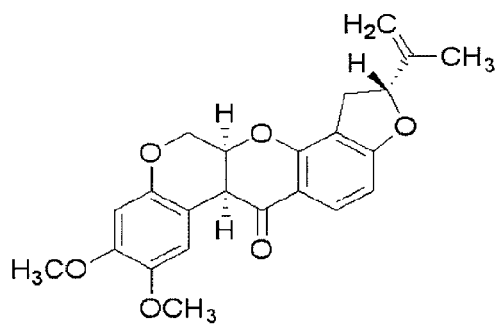
Rotenone
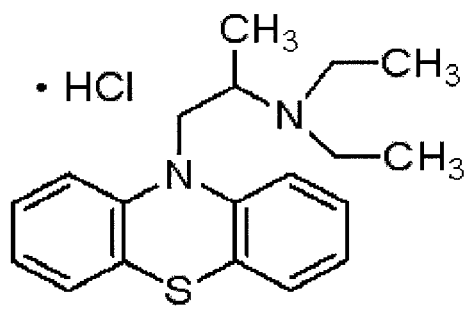
Ethopropazine hydrochloride
FIG. 10

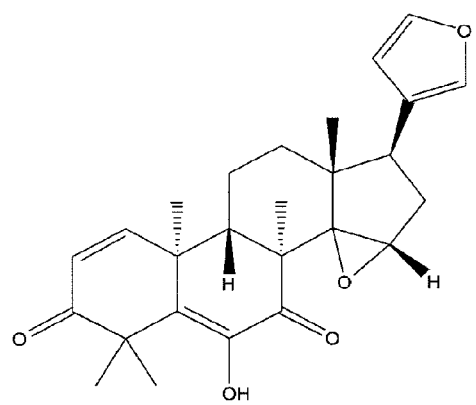
cedrelone
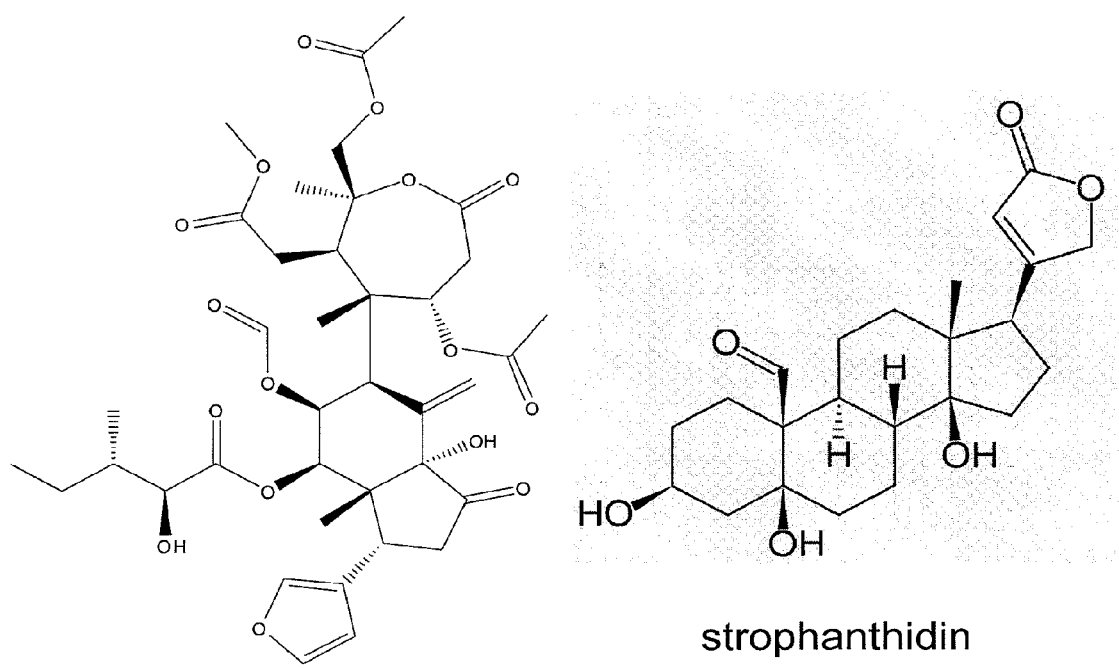
prieurianin
strophanthidin
FIG. 10 (cont.)

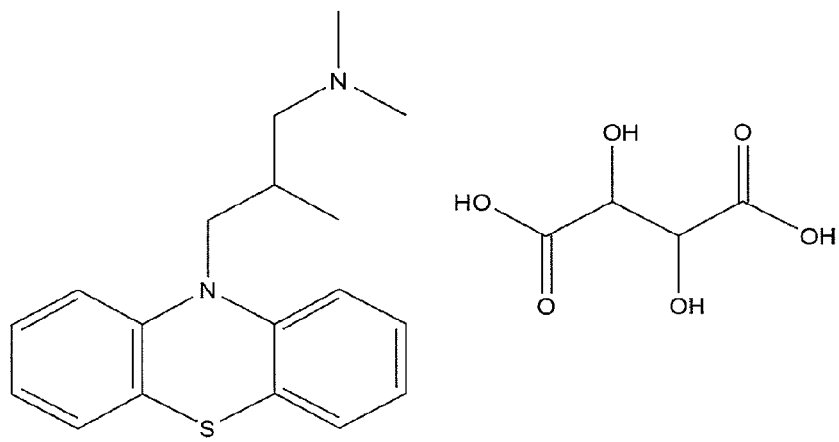
trimeprazine tartrate
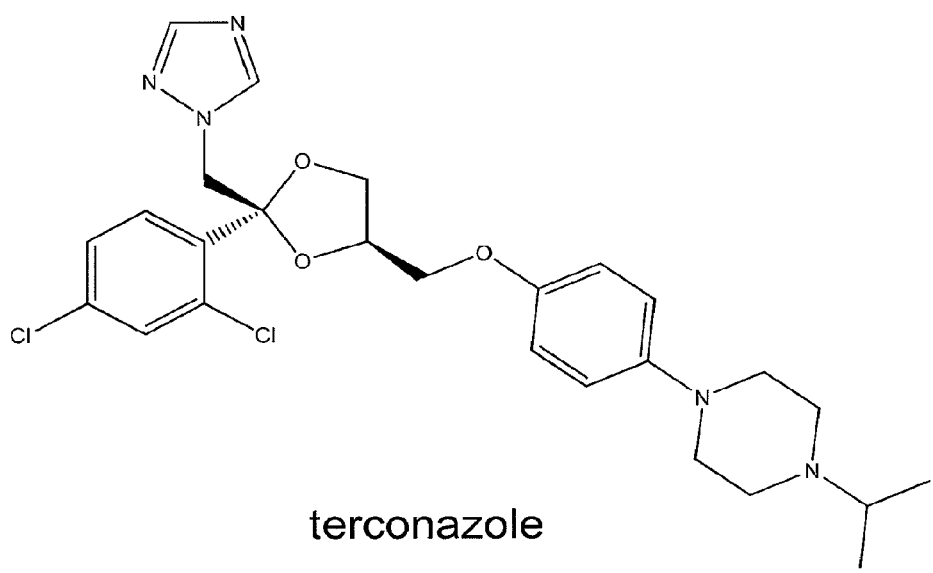
terconazole
FIG. 10 (cont.)

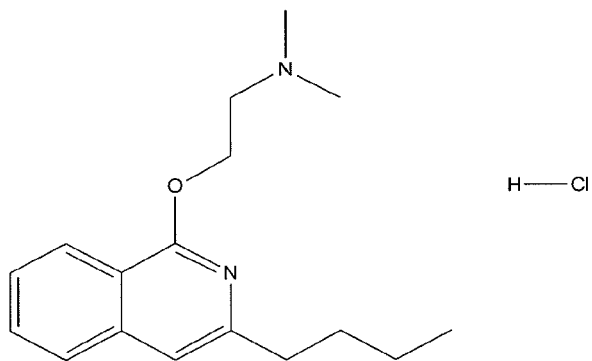
dimethisoquin hydrochloride
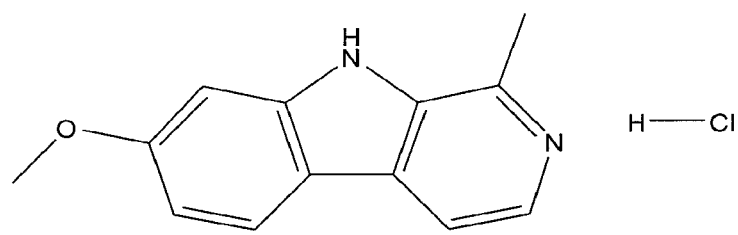
harmine hydrochloride
FIG. 10 (cont.)

COMPOSITIONS AND METHODS FOR PROMOTING THE GENERATION OF PDX1+ PANCREATIC CELLS

This application is a continuation of U.S. application Ser. No. 12/989,284, filed Dec. 6, 2010 (now U.S. Pat. No. 8,728,812), which is a national stage filing under 35 U.S.C. 371 of International Application No. PCT/US2009/41381, filed Apr. 22, 2009, which claims benefit under 35 U.S.C. §119(e) of the U.S. Provisional Application No. 61/047,056, filed Apr. 22, 2008. The contents of which are incorporated herein by reference in their entirety. International Application No. PCT/US2009/41381 was published under PCT Article 21(2) in English.

TECHNOLOGICAL FIELD

Certain embodiments disclosed herein relate generally to stem cells. More particularly, certain examples disclosed herein relate to pancreatic cells and pancreatic cell precursors produced by exposing human embryonic stem cells, or endoderm derived therefrom, to one or more small molecule compounds.

BACKGROUND

As of 2008, the American Diabetes Association estimates that about 7% of the population in the United States has diabetes, a disease in which the body does not produce or properly use insulin. Type 1 diabetes results from the body's inability to produce insulin, and Type 2 diabetes results from insulin resistance and lowered levels of insulin. A typical treatment for diabetes involves blood sugar level monitoring and insulin administration. There remains a need for better ways of treating diabetes.

SUMMARY

In one aspect, the invention features a method of producing a pancreatic cell or pancreatic cell precursor, the method comprising exposing a stem cell to an effective amount of at least one compound listed in Table I (e.g., Compound I) to differentiate the stem cell into the pancreatic cell or the pancreatic cell precursor.

In some embodiments, the stem cell is a human stem cell. In some embodiments, the stem cell is an embryonic stem cell (e.g., a human embryonic stem cell).

In some embodiments, a plurality of stem cells are differentiated into a plurality of pancreatic cells or pancreatic cell precursors. In some embodiments, the method also includes isolating a population of the pancreatic cells or the pancreatic cell precursors (e.g., wherein at least 5%, 10%, 15%, 20%, 25%, 30%, 50%, 75%, or greater are of the subject cell type).

In some embodiments, the method includes exposing the stem cell to at least one additional agent (e.g., FGF10).

In some embodiments, the pancreatic cell or the pancreatic cell precursor is a Pdx1+ cell. In some embodiments, the expression of a marker selected from the group consisting of: Pdx1, HNF6, Ptfla, Sox9, FoxA2, Nkx2.2, Ngn3, and Nkx6.1 is upregulated to by a statistically significant amount in the pancreatic cell or pancreatic cell precursor relative to the stem cell.

In some embodiments, the method also includes implanting the pancreatic cell or the pancreatic cell precursor into a subject (e.g., a subject having diabetes such as type I diabetes). In some embodiments, the stem cell is from the subject. In some embodiments, the stem cell is from a donor different than the subject (e.g., a relative of the subject).

In some embodiments, the stem cells are first differentiated to endoderm and then exposed to the at least one compound listed in Table I to provide the pancreatic cells or the pancreatic cell precursors.

In some embodiments, the method also includes directing the pancreatic cell or the pancreatic cell precursor to form an endocrine progenitor cell. In some embodiments, the method also includes implanting the endocrine progenitor cell into a subject (e.g., a subject having diabetes such as type I diabetes). In some embodiments, the stem cell is from the subject. In some embodiments, the stem cell is from a donor different than the subject (e.g., a relative of the subject).

In some embodiments, the method also includes directing the pancreatic cell or the pancreatic cell precursor to form an insulin+ beta cell. In some embodiments, the method also includes implanting the insulin+ beta cell into a subject (e.g., a subject having diabetes such as type I diabetes). In some embodiments, the stem cell is from the subject. In some embodiments, the stem cell is from a donor different than the subject (e.g., a relative of the subject).

In one aspect, the invention features a pancreatic cell or pancreatic cell precursor produced by exposing a stem cell to at least one compound listed in Table I (e.g., Compound I). In some embodiments, the stem cell is a human stem cell. In some embodiments, the stem cell is an embryonic stem cell (e.g., a human embryonic stein cell).

In some embodiments, the pancreatic cell or the pancreatic cell precursor is a Pdx1+ cell. In some embodiments, the expression of a marker selected from the group consisting of: Pdx1, HNF6, Ptfla, Sox9, FoxA2, Nkx2.2, Ngn3, and Nkx6.1 is upregulated to by a statistically significant amount in the pancreatic cell or pancreatic cell precursor relative to a stem cell.

In some embodiments, the pancreatic cell or pancreatic cell precursor is produced by exposing the stem cell to the at least one compound in combination with at least one additional agent (e.g., FGF10).

In some embodiments, the stem cell is first differentiated to endoderm prior to exposure to the at least one compound listed in Table I (e.g., Compound I).

In one aspect, the invention features a kit. The kit includes the following:
 a stem cell;
 at least one compound listed in Table I (e.g., Compound I); and
 instructions for culturing the stem cell and the at least compound to produce a pancreatic cell or a pancreatic cell precursor.

In some embodiments, the stem cell is a human stem cell. In some embodiments, the stem cell is an embryonic stem cell (e.g., a human embryonic stem cell).

In some embodiments, the pancreatic cell or the pancreatic cell precursor is a Pdx1+ cell. In some embodiments, the expression of a marker selected from the group consisting of: Pdx1, HNF6, Ptfla, Sox9, FoxA2, Nkx2.2, Ngn3, and Nkx6.1 is upregulated to by a statistically significant amount in the pancreatic cell or pancreatic cell precursor relative to a stem cell.

In some embodiments, the kit includes at least one additional agent (e.g., FGF10). In some embodiments, the stem cell is differentiated to endoderm prior to packaging in the kit.

In one aspect, the invention features a method of facilitating differentiation of a stem cell to a pancreatic cell or pancreatic cell precursor comprising providing a stem cell and providing at least one compound as listed in Table I (e.g., Compound I) to differentiate the stem cell to provide the pancreatic cell or the pancreatic cell precursor upon exposure of the stem cell to the at least one compound.

In some embodiments, the stem cell is a human stem cell. In some embodiments, the stem cell is an embryonic stem cell (e.g., a human embryonic stem cell).

In some embodiments, the pancreatic cell or the pancreatic cell precursor is a Pdx1+ cell. In some embodiments, the expression of a marker selected from the group consisting of: Pdx1, HNF6, Ptfla, Sox9, FoxA2, Nkx2.2, Ngn3, and Nkx6.1 is upregulated by a statistically significant amount in the pancreatic cell or pancreatic cell precursor relative to a stem cell.

In some embodiments, a plurality of stem cells are differentiated into a plurality of pancreatic cells or pancreatic cell precursors. In some embodiments, the method also includes isolating a population of the pancreatic cells or the pancreatic cell precursors (e.g., wherein at least 5%, 10%, 15%, 20%, 25%, 30%, 50%, 75%, or greater are of the subject cell type).

In some embodiments, the method includes at least one additional agent (e.g., FGF10).

In some embodiments, the stem cell has been differentiated to endoderm.

In some embodiments, the method also includes implanting the pancreatic cell or the pancreatic cell precursor into a subject (e.g., a subject having diabetes such as type I diabetes). In some embodiments, the stem cell is from the subject. In some embodiments, the stem cell is from a donor different than the subject (e.g., a relative of the subject).

In some embodiments, the method also includes implanting the endocrine progenitor cell into a subject (e.g., a subject having diabetes such as type I diabetes). In some embodiments, the stem cell is from the subject. In some embodiments, the stem cell is from a donor different than the subject (e.g., a relative of the subject).

In some embodiments, the method also includes directing the pancreatic cell or the pancreatic cell precursor to form an insulin+ beta cell. In some embodiments, the method includes implanting the insulin+ beta cell into a subject (e.g., a subject having diabetes such as type I diabetes). In some embodiments, the stem cell is from the subject. In some embodiments, the stem cell is from a donor different than the subject (e.g., a relative of the subject).

In one aspect, the invention features a method of facilitating differentiation of a stem cell to a pancreatic cell or pancreatic cell precursor comprising providing a culture medium comprising at least one compound listed in Table I (e.g., Compound I) to grow and differentiate the stem cell to provide the pancreatic cell or the pancreatic cell precursor.

In some embodiments, the stem cell is a human stem cell. In some embodiments, the stem cell is an embryonic stem cell (e.g., a human embryonic stem cell).

In some embodiments, the pancreatic cell or the pancreatic cell precursor is a Pdx1+ cell. In some embodiments, the expression of a marker selected from the group consisting of: Pdx1, HNF6, Ptfla, Sox9, FoxA2, Nkx2.2, Ngn3, and Nkx6.1 is upregulated by a statistically significant amount in the pancreatic cell or pancreatic cell precursor relative to a stem cell.

In some embodiments, a plurality of stem cells are differentiated into a plurality of pancreatic cells or pancreatic cell precursors. In some embodiments, the method also includes isolating a population of the pancreatic cells or the pancreatic cell precursors (e.g., wherein at least 5%, 10%, 15%, 20%, 25%, 30%, 50%, 75%, or greater are of the subject cell type).

In some embodiments, the method includes at least one additional agent (e.g., FGF10).

In some embodiments, the culture medium comprises a compound listed in Table I to differentiate human embryonic stem cells that have previously been differentiated to endoderm.

In some embodiments, the method also includes implanting the pancreatic cell or the pancreatic cell precursor into a subject (e.g., a subject having diabetes such as type I diabetes). In some embodiments, the stem cell is from the subject. In some embodiments, the stem cell is from a donor different than the subject (e.g., a relative of the subject).

In some embodiments, the method also includes implanting the endocrine progenitor cell into a subject (e.g., a subject having diabetes such as type I diabetes). In some embodiments, the stem cell is from the subject. In some embodiments, the stem cell is from a donor different than the subject (e.g., a relative of the subject).

In some embodiments, the method also includes directing the pancreatic cell or the pancreatic cell precursor to form an insulin+ beta cell. In some embodiments, the method also includes implanting the insulin+ beta cell into a subject (e.g., a subject having diabetes such as type I diabetes). In some embodiments, the stem cell is from the subject. In some embodiments, the stem cell is from a donor different than the subject (e.g., a relative of the subject).

In one aspect, the invention features a method of producing a pancreatic cell or pancreatic cell precursor from a stem cell, the method comprising culturing the stem in a medium comprising an effective amount of at least compound listed in Table I (e.g., Compound I) to promote differentiation of the stem cell into the pancreatic cell or pancreatic cell precursor.

In some embodiments, the stem cell is a human stem cell. In some embodiments, the stem cell is an embryonic stem cell (e.g., a human embryonic stem cell).

In some embodiments, the pancreatic cell or the pancreatic cell precursor is a Pdx1+ cell. In some embodiments, the expression of a marker selected from the group consisting of: Pdx1, HNF6, Ptfla, Sox9, FoxA2, Nkx2.2, Ngn3, and Nkx6.1 is upregulated by a statistically significant amount in the pancreatic cell or pancreatic cell precursor relative to a stem cell.

In some embodiments, a plurality of stem cells are differentiated into a plurality of pancreatic cells or pancreatic cell precursors. In some embodiments, the method also includes isolating a population of the pancreatic cells or the pancreatic cell precursors (e.g., wherein at least 5%, 10%, 15%, 20%, 25%, 30%, 50%, 75%, or greater are of the subject cell type).

In some embodiments, the method includes at least one additional agent (e.g., FGF10).

In some embodiments, the method also includes differentiating the human embryonic stem cells into endoderm prior to the culturing step.

In some embodiments, the method also includes implanting the pancreatic cell or the pancreatic cell precursor into a subject (e.g., a subject having diabetes such as type I diabetes). In some embodiments, the stem cell is from the subject. In some embodiments, the stem cell is from a donor different than the subject (e.g., a relative of the subject).

In one aspect, the invention features a method of producing a Pdx1+ pancreatic precursor comprising:
    differentiating a stem cell to provide an endoderm; and
    culturing the endoderm in the presence of an effective amount of at least one compound listed in Table I (e.g., Compound I) to produce the Pdx1+ pancreatic precursor.

In some embodiments, the stem cell is a human stem cell. In some embodiments, the stem cell is an embryonic stem cell (e.g., a human embryonic stem cell).

In some embodiments, the expression of a marker selected from the group consisting of: Pdx1, HNF6, Ptf1a, Sox9, FoxA2, Nkx2.2, Ngn3, and Nkx6.1 is upregulated by a statistically significant amount in the Pdx1+ pancreatic precursor relative to a stem cell.

In some embodiments, a plurality of stem cells are differentiated into a plurality of Pdx1+ pancreatic precursors. In some embodiments, the method also includes isolating a population of the Pdx1+ pancreatic precursors (e.g., wherein at least 5%, 10%, 15%, 20%, 25%, 30%, 50%, 75%, or greater are of the subject cell type).

In some embodiments, the method also includes implanting the Pdx1+ pancreatic precursor into a subject (e.g., a subject having diabetes such as type I diabetes).

In some embodiments, the method also includes differentiating the Pdx1+ pancreatic precursor into a mature pancreatic cell. In some embodiments, the method also includes implanting the mature pancreatic cell into a subject (e.g., a subject having diabetes such as type I diabetes). In some embodiments, the pancreatic cell is a beta cell.

In one aspect, the invention features a method of culturing a stem cell in culture medium, the method comprising treating the culture medium with a compound described in Table I, e.g., compound I. In some embodiments, the compound described in Table I, e.g., Compound I, is formulated into a preparation suitable for administration to a cell culture. In some embodiments, the stem cell is cultured for a time sufficient to differentiate into a pancreatic cell or a pancreatic cell precursor. In some embodiments, the stem cell is cultured for a time sufficient to upregulate the expression of a marker selected from the group consisting of Pdx1, HNF6, Ptf1a, Sox9, FoxA2, Nkx2.2, Ngn3, and Nkx6.1 by a statistically significant amount.

In one aspect, the invention features a preparation comprising a compound described in Table I (e.g., Compound I), wherein the preparation is suitable for administration to a cell culture.

In one aspect, the invention features an isolated cell population, isolated from a method described herein.

Additional aspects, features and examples are described in more detail below.

BRIEF DESCRIPTION OF THE FIGURES

Certain illustrative embodiments are described in more detail below with reference to the accompanying figures in which:

FIG. 2a are the results of an efficacy curve for ILV;

FIG. 2b are the results of ILV's effect on a HUES8-derived population with DMSO treated condition and Day 1 used as negative controls;

FIG. 2c are the results of FGF10 promoting ILV's effect;

μM PD098059 or 10 μM U0126 in the presence of 300 nM ILV for 4 days and stained with Pdx1 antibody;

FIG. 9 shows Table I which includes a list of compounds (Compounds I-XXI); and

FIG. 10 shows the chemical formulae of Compounds I-XXI listed in Table I of FIG. 9.

DETAILED DESCRIPTION

Certain embodiments disclosed herein describe the generation of pancreatic lineage cells by exposing stem cells to one or more compounds such as, for example, small molecule compounds. Certain examples of the technology provide significant advantages including, but not limited to, the ability to produce pancreatic cells and pancreatic cell precursors at low cost, easier and simplified production of pancreatic cells and pancreatic cell precursors using small molecules, and increased efficiency in generating pancreatic cells and pancreatic cell precursors from stem cell lines. One advantage of the technology described herein is the production of Pdx1+ pancreatic precursors by exposure to small molecule compounds. These and other advantages will be recognized by the person of ordinary skill in the art, given the benefit of this disclosure.

Stem cells are cells that retain the ability to renew themselves through mitotic cell division and can differentiate into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

While certain embodiments are described below in reference to the use of stem cells for producing pancreatic cells, germ cells may be used in place of, or with, the stem cells to provide pancreatic cells using similar protocols as the illustrative protocols described herein. Suitable germ cells can be prepared, for example, from primordial germ cells present in human fetal material taken about 8-11 weeks after the last menstrual period. Illustrative germ cell preparation methods are described, for example, in Shamblott et al., Proc. Natl. Acad. Sci. USA 95:13726, 1998 and U.S. Pat. No. 6,090,622.

Figure 1:
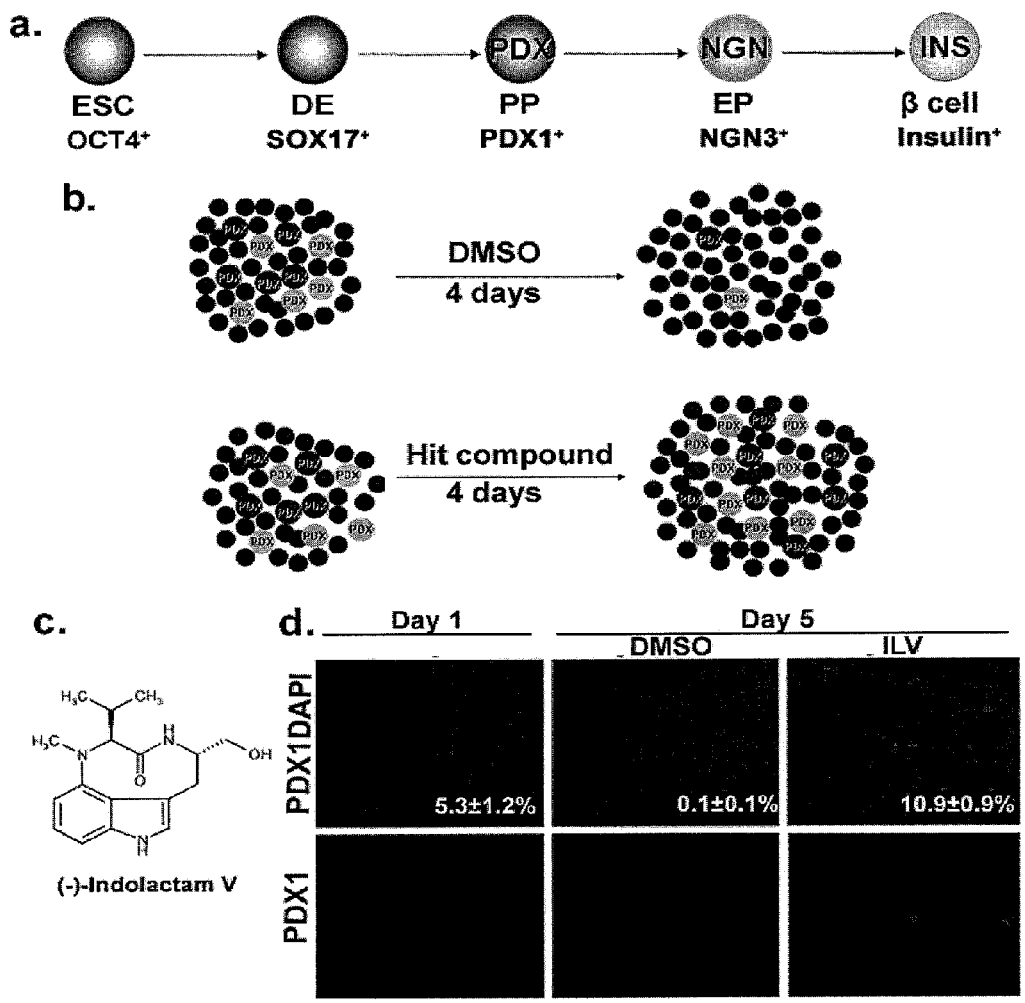
FIG. 1a shows a scheme of the stepwise differentiation from ESCs to β cells with DE representing definitive endoderm, PP representing pancreatic progenitor, EP representing endocrine progenitor, Ngn3 representing neurogenin 3, INS representing insulin.
FIG. 1b shows a scheme of a high throughput screen.
FIG. 1c shows a chemical structure of (−)-Indolactam V (ILV)
FIG. 1d are the results of ILV's effect on HUES9-derived population; Day 1 represents the population before chemical treatment; Day 5 DMSO represents the population treated with DMSO for 4 days; Day 5 ILV represents the population treated 1 μM ILV for 4 day.

Human embryonic stem cells (hESCs), with a virtually endless replication capacity and the potential to differentiate into most cell types, present, in principle, an unlimited starting material to generate the differentiated cells for clinical therapy (http://stemcells.nih.gov/info/scireport/2006report.htm, 2006). One possible application of hESCs is to generate new Beta cells for the cell replacement therapy of type I diabetics. Though several protocols have been reported to directly form insulin+ cells from ESCs, these produce precious few cells with demonstrable Beta cell phenotypes at the end of the protocols (Lumelsky et al., 2001; Rajagopal et al., 2003; Soria, 2001). By mimicking the signals used during embryonic development of pancreas, to the extent that they are known, a stepwise protocol is described herein to differentiate hESCs to functional Beta cells. This protocol involves directing ESCs first to form definitive endoderm, then Pdx1+ pancreatic progenitors, followed by formation of endocrine progenitors and, eventually, insulin+ β cells (FIG. 1a).

Studies in frogs, zebrafish and mice all pointed to the conclusion that signaling by members of the TGFβ family (specifically activin and nodal) is essential for vertebrate endoderm formation (Stainier, 2002). Studies suggest that signaling by activin (D'Amour et al., 2005; Kubo et al., 2004), Wnt (D'Amour et al., 2006), and PI3K-AKT (McLean et al., 2007) are all involved in the differentiation of ESCs to definitive endoderm. Extending these findings to in vitro differentiation, several groups have combined co-culture, changes in media, and growth factors to select for cells along the developmental pathway leading to islets and Beta cells (D'Amour et al., 2006; Jiang et al., 2007; Ku et al., 2004; Kubo et al., 2004). For example, D'Amour et al showed that treatment of hESCs with the combination of Wnt 3a and Activin A for 3 days, can result in ~70% of the cells expressing Sox17 (D'Amour et al., 2006), a marker for definitive endoderm. Certain embodiments described herein are directed to producing and identifying cells that express Pdx1 and have the capacity to form pancreatic cells.

Lineage tracing experiments and gene targeting of Pdx1 shows that embryonic Pdx1+ pancreatic progenitors are the common progenitor for the entire pancreas, forming duct, exocrine and endocrine tissues (Gu et al., 2003). Studies in chicks and zebrafish show that retinoic acid (RA) (Stafford and Prince, 2002), bone morphogenetic protein (BMP) (Tiso et al., 2002), and hedgehog (Hh) (diIorio et al., 2002; Roy et al., 2001) are involved in the generation of Pdx1+ pancreatic progenitors during embryogenesis. Furthermore, FGF10, which activates Notch signaling and blocks endocrine differentiation, has been implicated in the self-renewal of Pdx1+ pancreatic progenitors in vivo (Bhushan et al., 2001; Hart et al., 2003). Despite these advances in describing the in vivo formation of the pancreas, attempts to transfer this information to in vitro differentiation protocols have not resulted in efficient differentiation from ESCs to pancreatic progenitors. In most human ESC lines, only 5-10% of the differentiated cells are Pdx1+ with using current protocols (D'Amour et al., 2006; Jiang et al., 2007) and in some cases it is as few as 0.001% of the cells.

As an alternative to biological factors, cell-permeable small molecule compounds may be used as a means to control in vitro differentiation of ESCs (Chen et al., 2006; Ding and Schultz, 2004). Small molecule inducers would be less expensive, more easily controlled, and possibly more efficient than growth factors in directing differentiation. Certain embodiments described herein are directed to, or use, an image-based high throughput screen that uses a chemical library of 5000 compounds to identify small molecule compounds that can increase the number of Pdx1+ cells derived from hESCs.

In accordance with certain examples, pancreatic cells such as, for example, pancreatic endocrine cells (alpha cells, beta cells, delta cells, PP cells and the like) or pancreatic exocrine cells may be produced by exposing hESCs to one or more compounds listed in Table I. Human embryonic stem (hES) cells, are described, for example, by Cowan et al. (N Engl. J. Med. 350:1353, 2004) and Thomson et al. (Science 282: 1145, 1998); embryonic stem cells from other primates, such as Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998) may also be used in the methods disclosed herein. The stem cells may be, for example, unipotent, totipotent, multipotent, or pluripotent. In some examples, any cells of primate origin that are capable of producing progeny that are derivatives of at least one germinal layer, or all three germinal layers, may be used in the methods disclosed herein. In certain embodiments, pancreatic cell progenitors or precursors may be produced from the human embryonic stem cells. Pancreatic cell precursors refers to a cell that can be differentiated further, either in a single step or in multiple steps, to a mature pancreatic cell.

In certain examples, embryonic stem cells may be isolated, for example, as described in Cowan et al. (N Engl. J. Med. 350:1353, 2004) and U.S. Pat. No. 5,843,780 and Thomson et al., Proc. Natl. Acad. Sci. USA 92:7844, 1995. For example, hESCs cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hESCs include their pluripotent derivatives, such as primitive ectoderm-like (EPL) cells, as outlined, for example, in WO 01/51610 (Bresagen). hESCs can also be obtained from human pre-implantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses can be isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers. After 9 to 15 days, inner cell mass-derived outgrowths can be dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology can be individually selected by micropipette, mechanically dissociated into clumps, and replated. ES-like morphology is characterized as compact colonies with apparently high nucleus to cytoplasm ratio and prominent nucleoli. Resulting hESCs can then be routinely split every 1-2 weeks, for example, by brief trypsinization, exposure to Dulbecco's PBS (containing 2 mM EDTA), exposure to type IV collagenase (about 200 U/mL; Gibco) or by selection of individual colonies by micropipette. In some examples, clump sizes of about 50 to 100 cells are optimal.

In certain examples, the stem cells can be undifferentiated prior to exposure to the compounds disclosed herein, whereas in other examples it may be desirable to differentiate the stem cells to one or more intermediate cell types prior to exposure of the compounds listed in Table I. For example, the stems cells may display morphological, biological or physical characteristics of undifferentiated cells that can be used to distinguish them from differentiated cells of embryo or adult origin. In some examples, undifferentiated cells may appear in the two dimensions of a microscopic view in colonies of cells with high nuclear/cytoplasmic ratios and prominent nucleoli. The stem cells may be themselves (for example, without substantially any undifferentiated cells being present) or may be used in the presence of differentiated cells. In certain examples, the stem cells may be cultured in the presence of suitable nutrients and optionally other cells such that the stem cells can grow and optionally differentiate. For example, embryonic fibroblasts or fibroblast-like cells may be present in the culture to assist in the growth of the stein cells. The fibroblast may be present during one stage of stem cell growth but not necessarily at all stages. For example, the fibroblast may be added to stem cell cultures in a first culturing stage and not added to the stem cell cultures in one or more subsequent culturing stages.

Illustrative methods for molecular genetics and genetic engineering that may be used in the technology described herein may be found, for example, in current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found, for example, in Current Protocols in Protein Science (J. E. Colligan et al. eds., Wiley & Sons); Current Protocols in Cell Biology (J. S. Bonifacino et al., Wiley & Sons) and Current protocols in Immunology (J. E. Colligan et al. eds., Wiley & Sons). Illustrative reagents, cloning vectors, and kits for genetic manipulation may be commercially obtained, for example, from BioRad, Stratagene, Invitrogen, ClonTech, and Sigma-Aldrich Co.

Suitable cell culture methods may be found, for example, in Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Suitable tissue culture supplies and reagents are commercially available, for example, from Gibco/BRL, Nalgene-Nunc International, Sigma Chemical Co., and ICN Biomedicals.

In accordance with certain examples, step-wise differentiation may be implemented to differentiate stem cells to a desired cell, such as a pancreatic cell. One method of step-wise differentiation is described in U.S. Pat. No. 7,326,572. In brief, a first cell population enriched for a relevant committed common precursor cell may first be formed and then further differentiated into more mature cells that are more and more specialized towards the formation of certain types of pancreatic cells. Using this step-wise differentiation, hESC can be differentiated toward a mature cell type in several deliberate stages.

In certain embodiments, an immature endoderm cells may first be produced from undifferentiated hESCs. For examples, early in ontogeny, endoderm cells are capable of making epithelial cells of the GI tract and respiratory system, and the key digestive organs (liver and pancreas). Pancreatic cells can be generated using a two-stage approach. Stage 1 involves obtaining a population of common endoderm precursor cells. Stage 2 involves maturing the endoderm precursors into the pancreatic cells such as, for example, beta cells. In certain embodiments disclosed herein, the common endoderm precursor cells may be exposed to one or more compound shown in Table I to provide pancreatic cell precursors such as, for example, Pdx1$^+$ pancreatic cell precursors. hESCs can also be differentiated along the endoderm differentiation pathway by culturing with the suitable agents such as, for examples, the hepatocyte differentiation agent n-butyrate. A further description of the hepatocyte differentiation paradigm may be found in International Patent Publication WO 01/81549 (Geron Corporation). Sonic Hedgehog is thought to be involved in liver specification, so including cyclopamine (an inhibitor of Sonic Hedgehog) in the culture medium is thought to help divert the cells toward the pancreatic lineage. In some examples, differentiation may further be directed in a subsequent step, using, for example, the terminal differentiation factor nicotinamide (in the presence of cyclopamine and activin A). In other examples, one or more additional stages of differentiation may be implemented. For example, it may be desirable to further differentiate or mature of the pancreatic cells into a desired cell type.

In certain embodiments disclosed herein, the hESCs may be cultured or exposed to one or more compounds listed in Table I during any one or more stages of the step-wise differentiation. For example, it may be desirable to expose undifferentiated hESCs to at least one compound listed in Table I during the first stage of the step-wise differentiation, the second stage of step-wise differentiation and/or any additional stages of step-wise differentiation. In other examples, it may be desirable to expose the hESCs to at least one compound listed in Table I only after the first stage of step-wise differentiation.

In certain examples, the desired number of stages for producing pancreatic cell types may be based, at least in part, on the intended use of the end-stage cell populations. For example, it may be desirable to produce beta cell precursors for therapy for treating metabolic disorders. In other examples, it may be desirable to further differentiate the beta cell precursors into mature beta cells for use in treating diabetes.

In accordance with certain examples, several approaches may be used to differentiate the hESCs to endoderm cells. In one approach, the hESCs may be plated onto a new substrate or the medium may be exchanged to remove extracellular matrix or soluble factors that inhibit differentiation. This is sometimes referred to as the "direct differentiation method", and is described in general terms in International patent publication WO 01/51616, and U.S. Patent Publication 20020019046. It is usually preferable in the direct differentiation method to begin with a feeder-free culture of hESCs, so as to avoid potential complications in the differentiation process caused by residual feeder cells. Another approach is to put undifferentiated hESCs in suspension culture, which will frequently cause them to form aggregates of differentiated and undifferentiated cells. For example, hESCs can be harvested by brief collagenase digestion, dissociated into clusters, and passaged in non-adherent cell culture plates. The aggregates can be fed every few days, and then harvested after a suitable period, typically 4-8 days. In some instances, differentiation may take place in the presence of one or more of the compounds listed in Table I. Depending on the conditions, aggregates generally start by forming a heterogeneous population of cell types, including a substantial frequency of endoderm cells. The aggregates can then be dispersed and replated for the next stage in the differentiation process, on substrates such as laminin or fibronectin; or passaged in suspension culture using, for example, non-adherent plates and a suitable medium.

Direct differentiation or differentiation in aggregates can be monitored for the presence of endoderm cells using suitable markers such as those listed in U.S. Pat. No. 7,326,572. Once a sufficient proportion of endoderm is obtained, cells can be replated or otherwise manipulated to begin another stage of differentiation. In certain circumstances, differentiation or maintenance of cells may be enhanced if the cells are kept in micromass clusters (for example, 50 to 5,000 cells), so that alpha, beta, and delta cells can interact directly. Once the common progenitor cells are produced, these cells may be cultured, or exposed, to one or more compounds listed in Table I to differentiate the cells further.

In some examples, the hESCs (either undifferentiated or differentiated to endoderm) may be exposed only to one or more of the compounds listed in Table I, whereas in other examples, the hESCs (either undifferentiated or differentiated to endoderm) may be exposed to one or more compounds listed in Table I in combination with other compounds or factors including, but not limited to cyclopamine, TGF family members (TGF-alpha., Activin A, Activin B, TGF-beta-1, TGF-beta-3), exendin 4, nicotinamide, n-butyrate, DMSO, all-trans retinoic acid, GLP-1, bone morphogenic proteins (BMP-2, BMP-5, BMP-6, BMP-7), insulin-like growth factors (IGF-I, IGF-II), fibroblast growth factor (FGF7, FGF10, bFGF, FGF4), other growth factors (EGF, betacellulin, growth hormone, HGF), other hormones (prolactin, cholecytokinin, gastrin I, placental lactogen), TGF-beta. family antagonists (Noggin, follistatin, chordin), IBMX, wortmannin, dexamethazone, Reg, INGAP, cAMP or cAMP activators (forskolin), and/or extracellular matrix components (laminin, fibronectin).

In certain examples, the agents and hESCs may be used to produce pancreatic cells or pancreatic cell precursors by exposing the hESCs to an effective amount of at least one compound listed in Table I to differentiate the human embryonic stem cells into the pancreatic cells or the pancreatic cell precursors. The exact amount and type of compound used may vary depending on the number of cells, the desired differentiation stage and the number of prior differentiation stages that have been performed. In certain examples, the compound may be present in an effective amount. As used herein, "effective amount" refers to the amount of the compound that should be present to provide some degree of differentiation of the hESCs or further differentiation of partially differentiated hESCs such as those subjected to one or more previous differentiation stages. In additional examples, the compound may be present in the culture medium of the hESCs or may be added to the hESCs' during some stage of growth. In some examples, Compound I is used to produce the pancreatic cells or pancreatic cell precursors, and Compound I may be present in a concentration of about 10 micromoles/liter or less, for example about 1 micromole/liter or less. In certain examples, the stem cells may be exposed to the compound prior to any differentiation or during the first stage of differentiation, whereas in other examples, the stem cell may first be differentiated to an intermediate cell type such as, for example, endoderm, and then exposed to the compound.

In certain embodiments, a kit is provided for producing the pancreatic cells or pancreatic cell precursors. In certain examples, the kit comprises human embryonic stem cells, at least one compound listed in Table I, and instructions for using the stem cells and the at least one compound to produce a pancreatic cell or a pancreatic cell precursor. In some examples, the kit may further include media, substrates or other materials and components that may be useful in growing the hESCs and/or in differentiating the hESCs. In certain embodiments, the kit may comprise hESCs and Compound I of Table I.

In certain examples, a method of facilitating differentiation of human embryonic stem cells to pancreatic cells or pancreatic cell precursors is provided. In some examples, the method comprises providing human embryonic stem cells and providing at least one compound listed in Table I to differentiate the human embryonic stem cell to provide the pancreatic cell or the pancreatic cell precursor upon exposure of the stem cell to the compound. In certain examples, the compound may be present in an effective amount in the culture medium or may be added to the culture medium at a desired stage. In some examples, the compound may be Compound I of Table I. In certain examples, the stem cells may be exposed to the compound prior to any differentiation or during the first stage of differentiation, whereas in other examples, the stem cell may first be differentiated to an intermediate cell type such as, for example, endoderm, and then exposed to the compound.

In certain embodiments, a method of producing pancreatic cells or pancreatic cell precursors from human embryonic stem cells is disclosed. In one example, the method comprises culturing the human embryonic stem cells in a medium comprising an effective amount of at least one compound listed in Table I to cause differentiation of said cells into pancreatic cells or pancreatic cell precursors. In certain examples, the compound may be Compound I listed in Table I. In some embodiments, the stem cells may be cultured in the presence of the compound prior to any differentiation or during the first stage of differentiation, whereas in other examples, the stem cell may first be differentiated to an intermediate cell type such as, for example, endoderm, and then cultured in the presence of the compound.

In certain examples, a method of producing Pdx1$^+$ pancreatic precursors culturing human embryonic stem cells in the presence of an effective amount of Compound I in Table I to thereby produce the Pdx1$^+$ pancreatic precursors is provided. The hESCs may be any of those discussed herein or other suitable stem cells. Compound I may be present in the culture medium of the stem cells or may be added in bolus or periodically during growth of the stem cells. In certain examples, the stem cells may be exposed to the compound prior to any differentiation or during the first stage of differentiation, whereas in other examples, thy stem cell may first be differentiated to an intermediate cell type such as, for example, endoderm, and then exposed to the compound to provide the Pdx1+ pancreatic precursors.

In certain examples, a high content screening method is provided. In some examples, the method comprises exposing stem cells to at least one compound and determining if the compound increases the production of Pdx1$^+$ pancreatic precursor cells from the stem cells. In some examples, the stem cells may be differentiated prior to exposure to the library. In other examples, two or more compounds may be used, either individually or together, in the screening assay. In additional examples, the stem cells may be placed in a multi-well plate, and a library of compounds may be screened by placing the various members of the library in different wells of the multi-well plate. Such screening of libraries can rapidly identify compounds that are capable of producing Pdx1+ pancreatic precursor cells from the stem cells.

Certain specific examples are described below to illustrate and describe further some novel features of the technology described herein.

In one embodiment, the cells described herein are transplantable, e.g., they can be administered to a subject, e.g., a subject that was the source of the cells, or a different subject, e.g., a subject suffering from diabetes such as type I diabetes, or a normal subject. For example, the cells can be a form suitable for transplantation, e.g., organ transplantation.

The method can further include administering the cells to a subject in need thereof, e.g., a mammalian subject, e.g., a human subject. The source of the cells can be a mammal, preferably a human. The source or recipient of the cells can also be a non-human subject, e.g., an animal model. The term "mammal" includes organisms, which include mice, rats, cows, sheep, pigs, rabbits, goats, horses, monkeys, dogs, cats, and preferably humans. Likewise, transplantable cells can be obtained from any of these organisms, including a non-human transgenic organism. In one embodiment, the transplantable cells are genetically engineered, e.g., the cells include an exogenous gene or have been genetically engineered to inactivate or alter an endogenous gene.

A cells can be administered to a subject using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Example 1 hESC Culture and Differentiation

HUES2, HUES4, HUES8 and HUES9 cells can be routinely cultured on irradiated CF-1 MEF feeder cells in Knock-Out DMEM (Invitrogen) supplemented with 10% KnockOut Serum Replacement (Invitrogen), 10% human plasma fraction (Bayer Corp.), 2 mM L-glutamine (L-Glu, Invitrogen), 1.1 mM 2-mercaptoethanol (Invitrogen), 1 mM nonessential amino acids (Invitrogen), 1×penicillin/streptomycin (PS, Invitrogen) and 10 ng/ml bFGF (Invitrogen). Cells are passaged at the ratio of 1:10-1:12 every 5 days by using 1 mg/ml collagenase type IV (Invitrogen).

To generate a starting population, HUES cells were cultured on MEF feeder cells until 80-90% confluent, then treated with 25 ng/ml Wnt3a (R&D systems)+100 ng/ml Activin A (R&D systems) in advanced RPMI (A-RPMI, Invitrogen) supplemented with 1×L-Glu and 1×PS for 1 day, and then 100 ng/ml Activin A in A-RPMI supplemented with 1×L-Glu, 1×PS and 0.2% FBS (Invitrogen). Two days later, the media was changed to 50 ng/ml FGF10 (R&D systems)+0.25 µM KAAD-CYC (Calbiochem) in A-RPMI supplemented with 1×L-Glu, 1×PS and 2% FBS and maintained for additional 2 days. Cells were then transferred to 50 ng/ml FGF10+0.25 µM KAAD-CYC+2 µM RA (Sigma) in DMEM supplemented with 1×L-Glu, 1×PS, 1×B27 (Invitrogen) and cultured for an additional 4 days. ILV was obtained from Axxora, KAAD-CYC, TPB, PMA, BISI, Gö 6983, U0126 and PD98059 were obtained from Calbiochem and RA were obtained from Sigma.

For growth factor-induced differentiation, the ILV-treated populations were cultured in DMEM/F12 supplemented with 1×N2 (Invitrogen), 2 mg/ml albumin fraction V (Invitrogen), and 10 ng/ml bFGF (Invitrogen) for the first 4 days. 10 mM nicotinamide (Sigma) was then added and maintained for additional 8 days, changing the media every 3 days.

Example 2

Mouse Embryonic Stem Cell Culture and Differentiation

Mouse embryonic stem cells (mESCs) with Pdx1-GFP reporter are routinely cultured on irradiated CF-1 MEF feeder cells in KnockOut DMEM (Invitrogen) supplemented with 15% FBS (Hyclone), 2 mM L-Glu, 1.1 mM 2-mercaptoethanol, 1 mM nonessential amino acids, 1×PS and 10$^3$ unit LIF (Chemicon). Cells are passaged at the ratio of 1:12 every 3 days by using 0.25% trypsin-EDTA (Invitrogen).

To generate a definitive endoderm population, mESCs were plated on gelatin-coated surface at 2500 cell/cm$^2$ after depletion of MEF feeder cells. Then, the cells were treated with 1000 ng/ml recombinant mouse Nodal (R&D systems) in A-RPMI supplemented with 1×L-Glu, 1×L-PS and 0.2% FBS for 5 days. To screen small molecules, the definitive endoderm population was treated with 300 nM ILV in DMEM supplemented with 1×L-Glu, 1×PS, 1×B27 for 6 days.

Example 3

High Throughput Screen

For a high throughput screen, the starting material was hESCs (HUES9 cells) that were induced to pancreatic lineage using a slightly modified version of previously published protocols (D'Amour et al., 2006; Jiang et al., 2007), as described in Example 1. After 9 days of stepwise differentiation, a heterogeneous population of cells was generated containing cells that stained strongly, weakly or not at all with a Pdx1 antibody. Any cell that stained with the Pdx1 staining antibody was counted as Pdx1$^+$ cells regardless of staining intensity. Together, the Pdx1$^+$ cells comprises 5.1±1.8% of the total cell number.

To carry out the screen, the cells were trypsinized and plated on 804G-coated 384-well plates at 6000 cells/well using chemically defined media (DMEM supplemented with 2 mM L-Glu, 1×PS, 1×B27). After overnight incubation, compounds were screened by adding them to provide a final concentration of 10 µM, 1 µM and 0.1 µM. Four days later, the cells were stained with Pdx1 antibody and the plates were analyzed with Opera high content screening system (PerkinElmer). No detectable difference was found between non-treated and DMSO-treated conditions, indicating that DMSO had no effect at the concentration used in the primary screen (1:2000).

Figure 7:
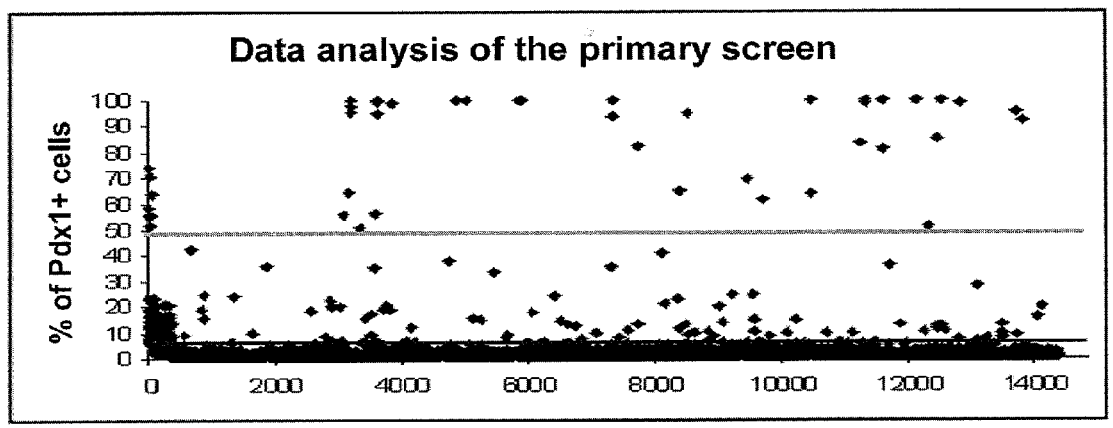
FIG. 7 shows a data analysis of the compound screening; points that are lower than green line (50%, the percentage of Pdx1+ cells) and higher than red line (7%, the percentage of Pdx1+ cells is 2 times higher than DMSO control) were selected as primary hits, and all points higher than green line (50%) are due to compound's autofluorescence.

The wells in which the percentage of Pdx1$^+$ cells is higher than present at day 1 and higher than day 5 treated with DMSO were selected as primary hits. Compounds that increase both the number and percentage of Pdx1$^+$ cells were picked as primary hits. Eleven compounds produced hits. (FIG. 7, Table I in FIG. 9 and formulas in FIG. 10). These eleven compounds were (−)-Indolactam V (FIG. 1c and Compound I in Table 1) boldine (Compound II), rotenone (Compound III), ethopropazine hydrochloride (Compound IV), cedrelone (Compound V), prieurianin (Compound VI), strophanthidin (Compound VII), trimeprazine tartrate (Compound VIII), terconazole (Compound IX), dimethisoquin hydrochloride (Compound X), harmine hydrochloride (Compound XI).

One compound, (−)-Indolactam V (ILV, FIG. 1c and Compound I of FIG. 9), shows a relatively strong effect and has a low effective concentration (~1 µM). The percentage of Pdx1$^+$ cells of ILV-treated population (10.9±0.9%) is higher than day 1 (5.3±1.2%) and DMSO-treated control at day 5 (0.1±0.1%, FIG. 1d).

Example 4

Quantitative RT-PCR

Total RNAs were extracted with the RNeasy Mini Kit (Qiagen) and reverse-transcribed using SuperScript III RT-PCR system (Invitrogen) according to the manufacturer's protocol. One microliter of cDNA sample was PCR amplified with QuantiFast SYBR Green PCR Kit (Qiagen) and analyzed with DNA engine Opticon2 (MJ Research).

Example 5

Illumina Microarray Analysis cRNA samples were prepared with an Illumina TotalPrep RNA Amplification Kit (Ambion). Data was acquired with an Illumina beadstation 500 (Illumina) and analyzed with beadstudio (Illumina).

Example 6

Immunocytochemistry

Cells were fixed with 10% formalin solution (Sigma) for 20 min at room temperature. Immunostaining was carried out with standard protocols. The following primary antibodies were used: goat anti-Pdx1 (1:500; R&D system); rabbit anti-FOXA2 (1:500; Upstate); rabbit anti-HNF6 (1:200; Santa Cruz Biotech); guinea pig anti-insulin (1:1000; Dako); rabbit anti-c-peptide (1:500; Linco); rabbit anti-amylase (1:200, Sigma); goat anti-HNF1β (1:100, Santa Cruz Biotech); and biotinylated DBA (1:400; Vector Lab). Alexa-488-, Alexa-555-, and Alexa-647-conjugated donkey antibodies against mouse, rabbit, guinea pig and goat, and Pacific Blue conjugate-streptavidin (Invitrogen) were used at 1:300 dilution.

Example 7

Kidney Capsule Implantation and Tissue Preparation

After 4 days treatment with 300 nM ILV or 300 nM ILV+ 50 ng/ml FGF10, the cells were washed with DPBS for 3 times and treated with 1 mg/ml dispase for 5 min at 37° C. Then, the cells were lifted with the help of cell scraper, collected by centrifugation and resuspended in 50 µl DMEM supplemented 1×B27. About 40 µl (~2×10$^6$ cells) of cell clumps were implanted into the left kidney of xylazine anesthetized CD1-nude mice. Two mice were prepared for each sample. Twelve weeks later, the left kidneys were dissected and fixed in 4% paraformaldehyde for 4 hours at 4° C. and processed by standard techniques to generate 15 micrometer cryosections for antibody staining. The antibodies were used as the same condition as immunocytochemistry. Fluorescent images were acquired on an inverted Zeiss LSM 510 confocal microscope.

Example 8

Western Blot Analysis

Cells were lysed in 1×RIPA lysis buffer (Upstate Biotechnology) with 1% protease inhibitor mixture (Sigma)/1% phosphatase inhibitor mixture (Sigma)/1% phosphatase inhibitor mixture II (Sigma). Proteins were separated by 4-20% Tris-Glycine SDS/PAGE (Biorad) under denaturing conditions and transferred to a nitrocellulose membrane. After blocking with 5% nonfat milk in DPBS, the membrane was incubated with primary antibodies against phospho-ERK1/2 (Thr-202/Tyr-204) (1:2,000, Sigma) and ERK1/2 (1:1,000, Cell Signaling) overnight at 4° C. The membrane was then washed, incubated with anti-mouse/rabbit peroxidase-conjugated affinity-purified secondary antibody (1:1000, Cell Signaling) at room temperature for 1 hour, and developed by SuperSignal chemiluminescence (Pierce).

Example 9

ILV Effects on Multiple hESC Lines and Mouse ESCs

Additional experiments were carried out to optimize treatment to obtain more Pdx1$^+$ cells. Titration of ILV from 20 nM to 5 µM showed that it functions in a dose-dependent manner ($EC_{50}$=142 nM, FIG. 2a) with its highest efficiency and no detectable toxicity at 300 nM. Secondly, since hESC lines vary in their differentiation potentials (Osafune et al., 2008), ILV was tested on other hESC lines and shown to be effective on HUES 2, 4 and 8. After 4 days treatment with ILV, 26.9±2.8% cells of HUES8-derived population are positively stained by Pdx1 antibody (FIG. 2b), making it the most responsive of the lines tested.

To optimize further the differentiation conditions, ILV was combined with mitogens that have been reported to be involved in pancreatic development, including FGF10 (Hart et al., 2003), Wnt3a (D'Amour et al., 2005), Activin A (D'Amour et al., 2005), Activin B (Frandsen et al., 2007), and KAAD-cyclopamine (KAAD-CYC, a potent analog of cyclopamine (Kim and Melton, 1998). The effect of ILV is significantly improved in the presence of FGF10. When the starting population is treated with the combination of 300 nM ILV and 50 ng/ml FGF10, after 4 days culture, 45.8±8.1% cells of HUES8-derived population are stained with Pdx1 antibody (FIG. 2c). If the starting population is only treated with FGF10, in the absence of ILV, only 5.7±2.3% of the population is Pdx1$^+$ cells (FIG. 2c), suggesting that ILV functions, at least partially, through an FGF10-independent mechanism.

Figure 3:
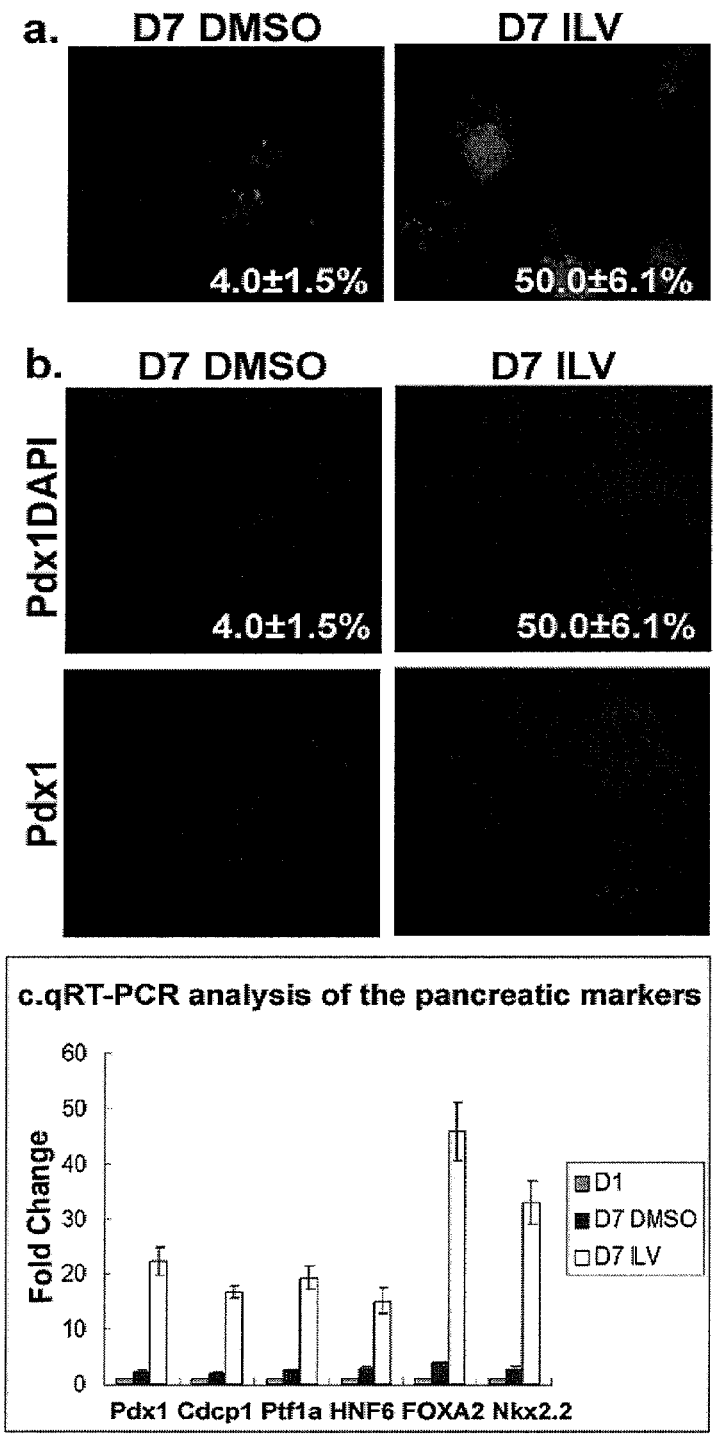
FIG. 3 are the results of experiments that demonstrate that ILV promotes the pancreatic differentiation of mouse embryonic stem cells.

To determine whether ILV functions on other species, the effect of ILV on a population of mouse ESCs (mESCs) that have been induced to form definitive endoderm was examined. The definitive endoderm population was derived from mESCs with Pdx1-GFP reporter (Micallef et al., 2005) using 5 day treatment with 1000 ng/ml Nodal and then treated with 300 nM ILV for additional 6 days. In the control (treated with DMSO) condition, only 4.0±1.5% cells of the population are GFP$^+$. After treatment with 300 nM ILV, the percentage of GFP$^+$ cells increases to 50.0±6.1% (FIG. 3a). The increase of Pdx1 expression can be further confirmed with immunostaining (FIG. 3b) and quantitative RT-PCR (qRT-PCR, FIG. 3c). In addition, the expression of mRNAs of the pancreatic markers, including Pdx1, Cdcp1, Ptf1a, HNF6, FOXA2, Nkx2.2 increase after ILV treatment (FIG. 3c). The effect of ILV on mESC-derived definitive endoderm suggests that ILV functions on two mammalian species and further confirms that some signals for pancreatic development are conserved between mouse and human.

Example 10

ILV-Treated Population Expresses Multiple Pancreatic Lineage Markers

Figure 4:
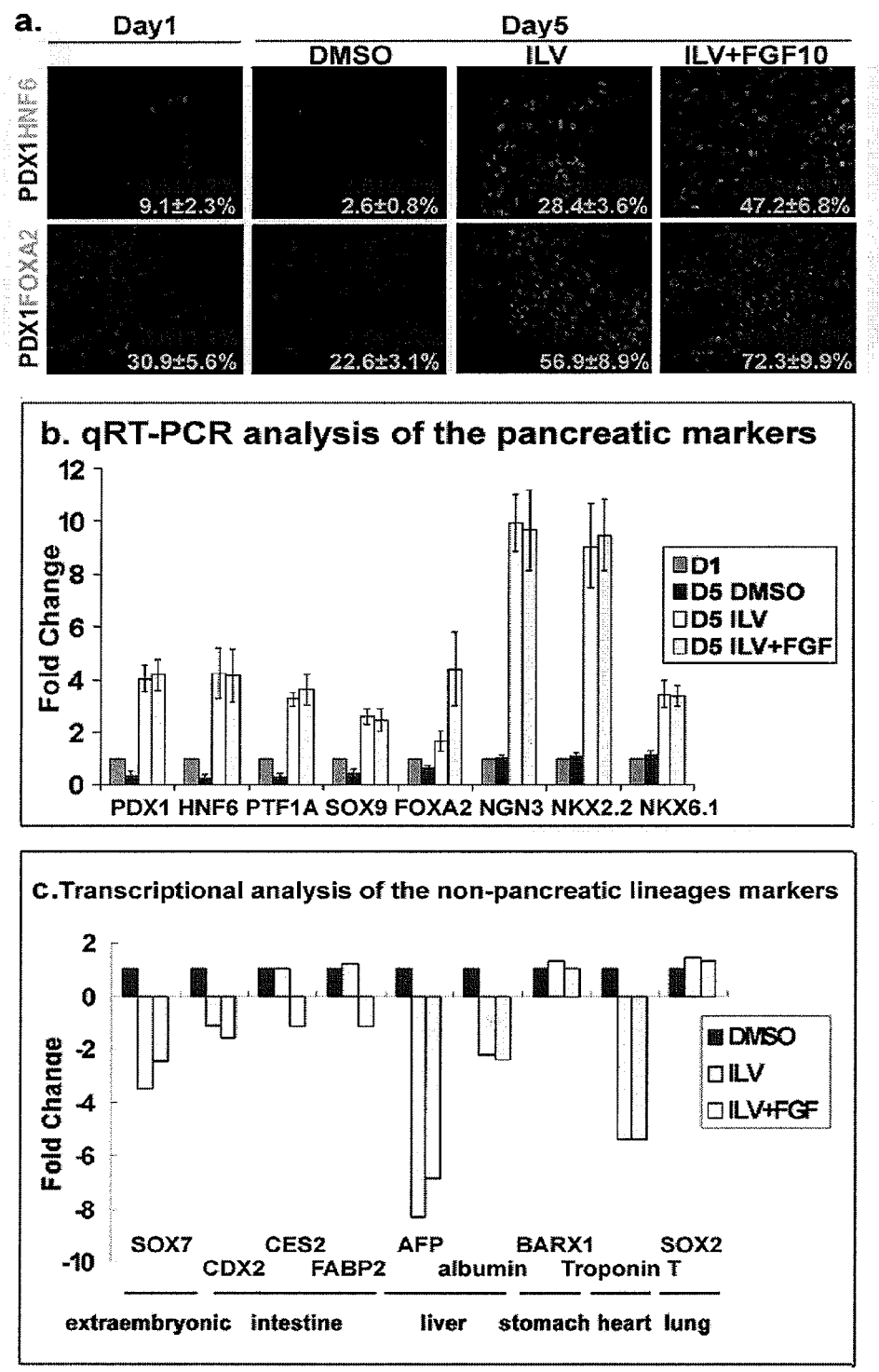
FIG. 4a are the results demonstrating that ILV-treated populations express multiple pancreatic markers.
FIG. 4b are the results of qRT-PCR analysis of the expression of the pancreatic markers in the ILV-treated population (300 nM ILV or 300 nM ILV+ 50 ng/ml FGF10 for 4 days and then analyzed with qRT-PCR. DMSO treatment condition) with day 1 used as a negative control.
FIG. 4c are the results of an Illumina microarray analysis of the markers expressed in non-pancreatic tissues (HUES8-derived population was treated with 300 nM ILV or 300 nM ILV+ 50 ng/ml FGF10 for 4 days and analyzed with Illumina) with DMSO treatment condition used as a negative control.

To further characterize the cells induced by ILV, beyond Pdx1$^+$ expression, multiple pancreatic lineage markers were examined by immunocytochemistry and qRT-PCR. More than 96% of the Pdx1$^+$ cells following ILV treatment show significant expression of other pancreatic progenitor markers, including FOXA2 and HNF6 (FIG. 4a). After ILV treatment, Pdx1, HNF6, Ptf1a, Sox9, FOXA2 mRNAs level increase (FIG. 4b). More interestingly, some endocrine progenitor markers, including Nkx2.2, Ngn3 and Nkx6.1, are upregulated as measured by qRT-PCR (FIG. 4b). Furthermore, the markers expressed in non-pancreatic tissues or organs (including Sox7 for extraembryonic endoderm, Cdx2, Ces2, and FABP2 for intestine, AFP and albumin for liver, BARX1 for stomach, Troponin T for heart, and Sox2 for lung) either decrease or do not significantly change as indicated by Illumina microarray analysis (FIG. 4c). Together these data show that the ILV-treated cells express more than just Pdx1 and express many genes in the pancreatic lineage.

Example 11

ILV-Treated Population Shows Improved Ability to Contribute to Exocrine, Endocrine and Duct Cells Both In Vitro and In Vivo In mouse embryonic development, Pdx1$^+$ pancreatic progenitors contribute to exocrine, endocrine and duct cells (Gu et al., 2003). The developmental potential of Pdx1$^+$ cells produced by ILV treatment was tested in two assays. First, following published protocols for in vitro differentiation (Jiang et al., 2007), cells were cultured with bFGF and nicotinamide for an additional 12 days. Using this in vitro differentiation assay, four different induced cell types were tested, including HUES8-derived population before ILV treatment (no treatment), the HUES8-derived population after 4 day treatment with DMSO, 300 nM ILV or 300 nM ILV+50 ng/ml FGF10, respectively. After 12 days culture with bFGF and nicotinamide, these four populations of cells were stained with the antibodies against insulin, c-peptide, amylase or DBA (a duct marker).

Figure 5:
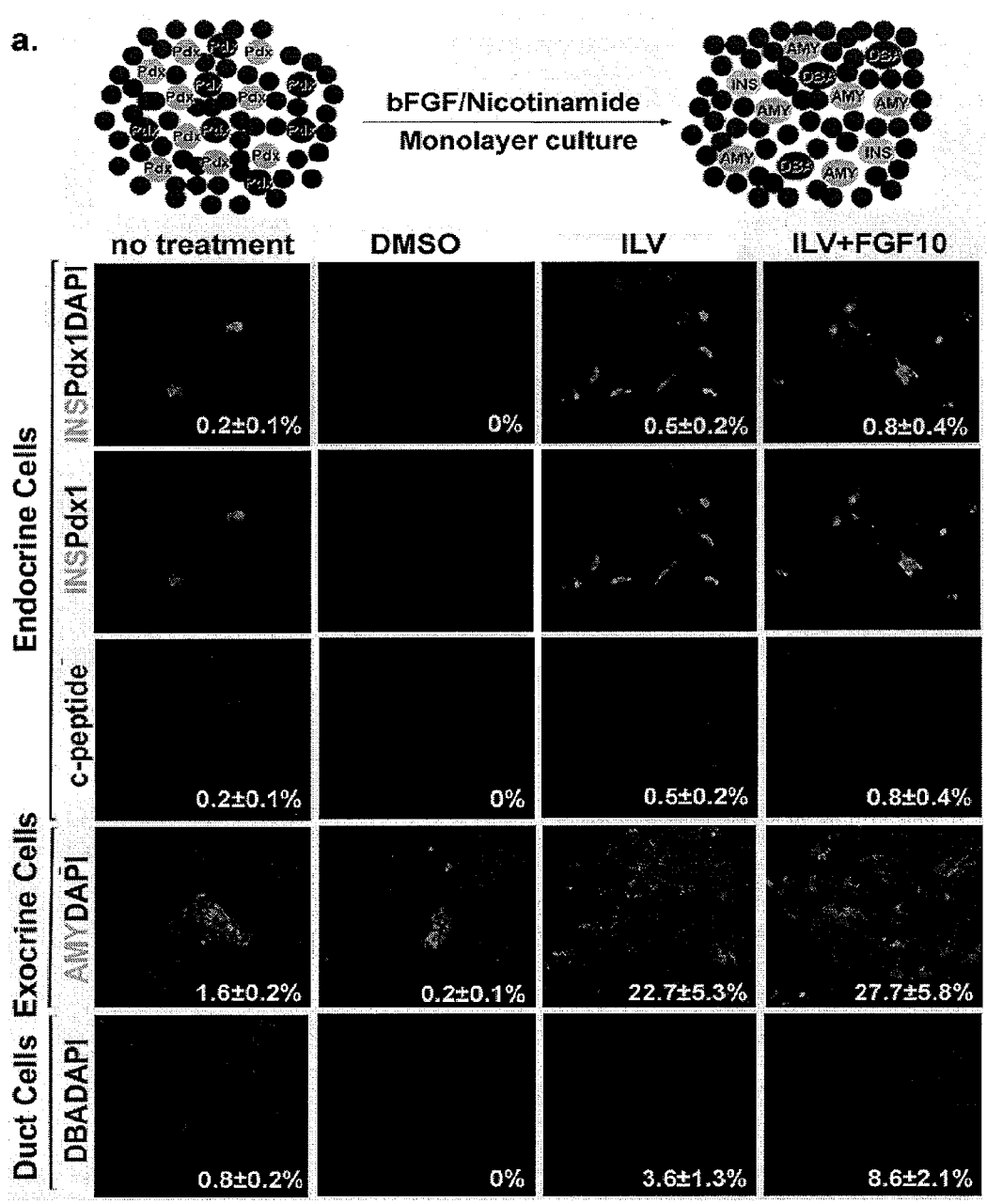
FIGS. 5a and 5b are immunocytochemistry and qRT-PCR results, respectively showing that ILV treatment improves the capacity of HUES8-derived population to differentiate into multiple pancreatic lineages in vitro and in vivo; the ILV-treated population can further differentiate into endocrine, exocrine and duct cells with additional growth factors treatment indicated by (a) immunocytochemistry and (b) qRT-PCR.
FIG. 5c are results showing that the ILV-treated population differentiates into endocrine and exocrine cells after injection under the kidney capsule of CD1-nude mice. After 4 days treatment with 300 nM ILV or 300 nM ILV+ 50 ng/ml FGF10, the cells were collected and implanted into the left kidney of CD1-nude mice. Twelve weeks later, the left kidneys were dissected to generate cryosections for antibody staining.

There were more insulin$^+$ cells detected in ILV-treated (0.5±0.2%) or ILV+FGF10 (0.8±0.4%)-treated population compared to DMSO-treated (0%) or no treatment population (0.2±0.1%) (FIG. 5a). All insulin$^+$ cells express c-peptide as well as Pdx1. Moreover, compared to no treatment or the DMSO-treated cells, the ILV-treated or ILV+FGF10-treated cells shows a stronger ability to contribute to other pancreatic lineages, including amylase$^+$ exocrine cells (no treatment: 1.6±0.2%; DMSO: 0.2±0.1%; ILV: 22.7±5.3%; ILV+FGF: 27.7±5.8%), DBA$^+$ duct cells (no treatment: 0.8±0.2%; DMSO: 0%; ILV: 3.6±1.3%; ILV+FGF: 8.6±2.1%, FIG. 5a) and somatostatin$^+$ cells indicated by immunostaining and qRT-PCR (FIG. 5b). Taken together, these results are consistent with ILV treatment increasing the capacity of hESC-derived cells to differentiate into multiple pancreatic lineages in vitro.

To further assess the developmental competence of chemically-treated cells, the cells were transplanted under the kidney capsule of nude mice, an assay used by others to observe pancreatic differentiation in vivo (Korsgren et al., 1991; Movassat et al., 2002). The grafts derived from ILV-treated or ILV+FGF10-treated population contained cell clusters that expressed endocrine markers, including insulin and c-peptide, and an exocrine marker, amylase (FIG. 5c). Additionally, all insulin$^+$ cells express c-peptide. In contrast, no insulin$^+$ cells were detected in the mice injected with DMSO-treated population. The presence of the insulin$^+$/c-peptide$^+$ or amylase$^+$ cell clusters is consistent with ILV-treated or ILV+FGF10-treated populations being capable of partially progressing through the pancreatic differentiation program in vivo. After twelve weeks, no evidence for teratoma was detected.

Example 12

ILV Functions Through Directing Pancreatic Differentiation of hESC-Derived Definitive Endoderm Population The results provided above are consistent with (1) ILV promotion of the proliferation or replication of the few pancreatic progenitors present in the starting population and with (2) differentiation induction of definitive endoderm by the compound. To distinguish between these possibilities, a HUES8-derived population was treated with 300 nM ILV for 4 days and analyzed for proliferation by staining with the antibody against Ki67 (marker for proliferating cells). The results show no Pdx1+ cells expressing Ki67 following treatment with ILV (FIG. 6a), a result inconsistent with the notion that ILV functions by promoting proliferation of pre-existing Pdx1+ cells.

ILV was next tested at different steps of the hESC differentiation process (see FIG. 1a). ILV was tested on the differentiation of HUES8 cells to definitive endoderm population, which was assessed by immunostaining with Sox17 antibody.

There was no detectable difference between ILV treatment and the control (DMSO) either in the presence or in the absence of Wnt3a/Activin (FIG. 6b), indicating that ILV does not directly cause or affect the differentiation from ESCs to definitive endoderm. Secondly, ILV was examined on the definitive endoderm population containing 70% Sox17+ cells derived from HUES8 by Wnt3a/Activin treatment (D'Amour et al., 2006). After 4 days culture, there were significantly more Pdx1+ cells detected in the ILV-treated conditions (21.5±2.4%) or ILV+FGF10 treated conditions (34.6±4.1%) than DMSO-treated conditions (2.8±0.6%, FIG. 6c). Thus, ILV functions by inducing pancreatic specification of hESC-derived definitive endoderm population.

Example 13

ILV Role in PKC Signaling

It has been reported that ILV activates protein kinase C (PKC) signaling in some cell lines (Heikkila and Akerman, 1989; Hirota et al., 1987). PKC is a family of serine/threonine kinases that regulates a very diverse set of cellular processes, including differentiation, proliferation, apoptosis, cell migration, and cell survival (Griner and Kazanietz, 2007).

Figure 6:
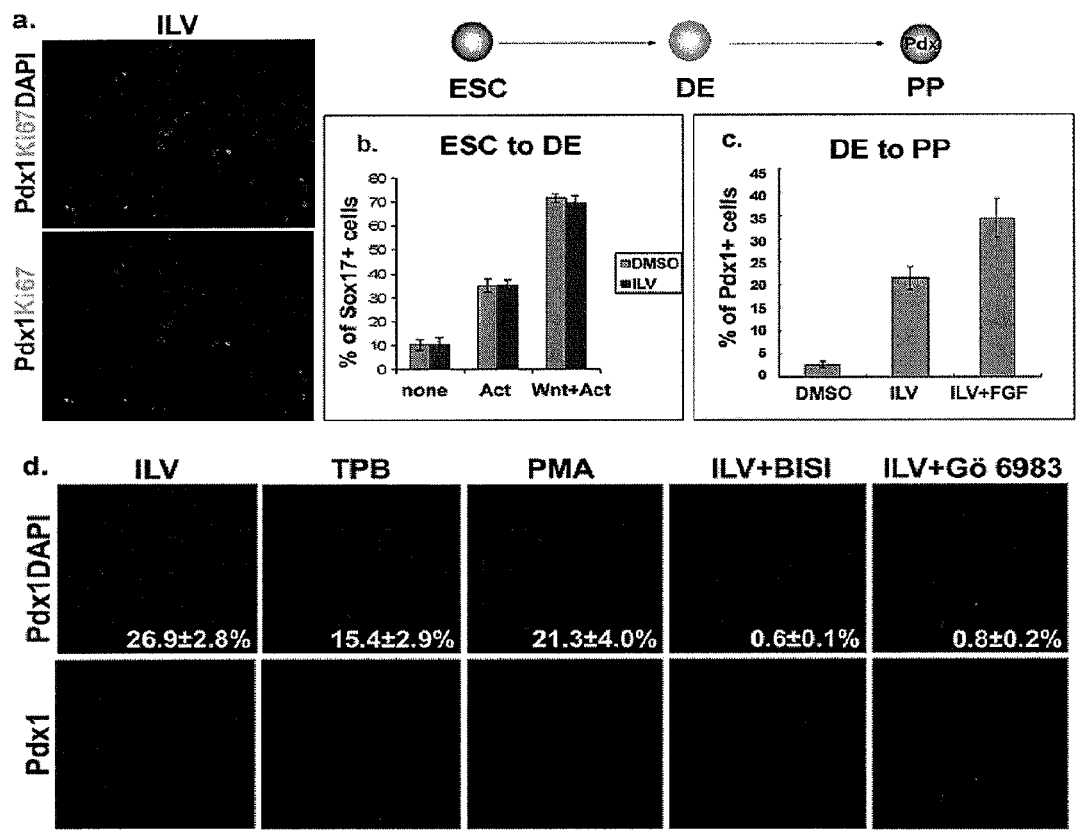
FIG. 6a are results showing that Pdx1+ cells following ILV treatment do not proliferate.
FIG. 6b are results showing ILV does not have effect on the differentiation from hESCs to definitive endoderm population (HUES8 cells were treated with 300 nM ILV in the presence or absence of Wnt3a and Activin A for 3 days and stained with the Sox17 antibody. None: in the absence of Wnt3a or Activin A for 3 days; Act: in the presence of 100 ng/ml Activin for 3 days; Wnt+Act: in the presence of 25 ng/ml Wnt3a and 100 ng/ml Activin A for 1 day and 100 ng/ml Activin A for additional two days)
FIG. 6c are results showing that ILV directs the specification of definitive endoderm population toward pancreatic lineage (definitive endoderm population was derived from HUES8 after 1 day treatment with 25 ng/ml Wnt3a and 100 ng/ml Activin A for 1 day and 100 ng/ml Activin A for additional 2 days; then, the definitive endoderm population was treated with 300 nM ILV or 300 nM ILV+50 ng/ml FGF10 for additional 4 days)
FIG. 6d are results showing ILV functions through PKC activation and that PKC agonists mimic ILV's effect and PKC antagonists block ILV's effect (HUES8-derived population was treated with 500 nM TPB or 14 nM PMA in the absence of ILV and 1 μM BISI or 10 μM Gö 6983 in the presence of 300 nM ILV for 4 days and stained with Pdx1 antibody)

To determine whether PKC signaling is being activated in HUES-derived cells, HUES8-derived definitive endoderm population was treated with two PKC agonists, TPB ((2S,5S)-(E,E)-8-(5-(4-(trifluoromethyl)phenyl)-2,4-pentadienoylamino)benzolactam) and PMA (phorbol-12-myristate-13-acetate), in the absence of ILV. Both PKC agonists mimic the effect of ILV. After 4 days treatment with 500 nM TPB or 14 nM PMA, the percentage of Pdx1+ cells increases to 15.4±2.9% and 21.3±4.0%, respectively (FIG. 6d), comparable to efficiency of Pdx1+ cells induced by ILV. Furthermore, HUES8-derived population was treated with two PKC antagonists, BISI (Bisindolylmaleimide I) and Gö 6983, in the presence of ILV. Either 1 μM BISI or 10 μM Gö 6983, both block ILV's effect, in which the percentage of Pdx1+ cells decreases from 26.9±2.8% to 0.6±0.1% and 0.8±0.2%, respectively (FIG. 6d). This suggests that ILV induces pancreatic differentiation of hESC-derived population through the activation of PKC signaling.

The PKC family has at least 11 isoforms, which are classified into three subgroups based on their mechanisms (Griner and Kazanietz, 2007). Gö6983, is not effective in suppressing PKCμ kinase activity (Gschwendt et al., 1996), but shows strong inhibition on ILV's effect. This data suggests that ILV does not function through PKCμ.

Figure 8:
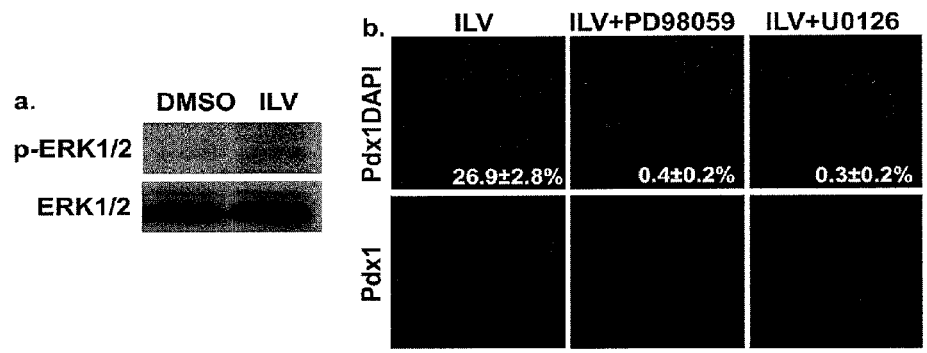
FIG. 8a are results showing that ILV activates ERK1/2 phosphorylation in HUES8-derived population. HUES8-derived population (treated with 300 nM ILV for 1 hour and analyzed with Western blotting)
FIG. 8b are results showing MEK/ERK inhibitors block ILV's effect; HUES8-derived population was treated with 50

Experiments were performed to monitor downstream signaling by PKC. Since ERK signaling has been reported to be regulated by PKC (Ueda et al., 1996), the activity of ERK signaling was examined with Western blotting to detect the phosphorylation of ERK1/2 at Thr-202/Tyr-204. After 1 hour treatment with 300 nM ILV, the phosphorylation of ERK1/2 increased compared to the DMSO-treated control (FIG. 8a). In addition, MEK/ERK inhibitors, PD098059 or U0126, both block ILV's effect. When HUES8-derived definitive endoderm population were treated with 300 nM ILV together with 50 μM PD098059 or 10 μM U0126, the percentage of Pdx1+ cells decreased from 26.9±2.8% to 0.4±0.2% (PD) or 0.3±0.2% (U0126) (FIG. 8b). These results suggest that ERK activation is involved when ILV is present Certain publications are referred to herein, and the full citation of at least some of these publication is provided below for convenience purposes.

Bhushan, A., Itoh, N., Kato, S., Thiery, J. P., Czernichow, P., Bellusci, S., and Scharfmann, R. (2001). Fgf10 is essential for maintaining the proliferative capacity of epithelial progenitor cells during early pancreatic organogenesis. Development 128, 5109-5117.

Chen, S., Do, J. T., Zhang, Q., Yao, S., Yan, F., Peters, E. C., Scholer, H. R., Schultz, P. G., and Ding, S. (2006). Self-renewal of embryonic stem cells by a small molecule. Proc Natl Acad Sci USA 103, 17266-17271.

Cowan, C. A., Klimanskaya, I., McMahon J., Atienza, J., Witmyer, J., Zucker, J. P., Wang, S., Morton, C. C., MsMahon A. P., Powers, D., Melton, D. A., Derivation of embryonic stem-cell lines from human blastocysts. N Engl J Med. 350, 353-356.

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-1541.

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. Nat Biotechnol 24, 1392-1401.

diIorio, P. J., Moss, J. B., Sbrogna, J. L., Karlstrom, R. O., and Moss, L. G. (2002). Sonic hedgehog is required early in pancreatic islet development. Dev Biol 244, 75-84.

Ding, S., and Schultz, P. G. (2004). A role for chemistry in stem cell biology. Nat Biotechnol 22, 833-840.

Frandsen, U., Porneki, A. D., Floridon, C., Abdallah, B. M., and Kassem, M. (2007). Activin B mediated induction of Pdx1 in human embryonic stem cell derived embryoid bodies. Biochem Biophys Res Commun 362, 568-574.

Griner, E. M., and Kazanietz, M. G. (2007). Protein kinase C and other diacylglycerol effectors in cancer. Nat Rev Cancer 7, 281-294.

Gschwendt, M., Dieterich, S., Rennecke, J., Kittstein, W., Mueller, H. J., and Johannes, F. J. (1996). Inhibition of protein kinase C mu by various inhibitors. Differentiation from protein kinase c isoenzymes. FEBS Lett 392, 77-80.

Gu, G., Brown, J. R., and Melton, D. A. (2003). Direct lineage tracing reveals the ontogeny of pancreatic cell fates during mouse embryogenesis. Mech Dev 120, 35-43.

Hart, A., Papadopoulou, S., and Edlund, H. (2003). Fgf10 maintains notch activation, stimulates proliferation, and blocks differentiation of pancreatic epithelial cells. Dev Dyn 228, 185-193.

Heikkila, J., and Akerman, K. E. (1989). (−)-Indolactam V activates protein kinase C and induces changes in muscarinic receptor functions in SH-SY5Y human neuroblastoma cells. Biochem Biophys Res Commun 162, 1207-1213.

Hirota, M., Suganuma, M., Yoshizawa, S., Horiuchi, T., Nakayasu, M., Hasegawa, M., Endo, Y., Shudo, K., and Fujiki, H. (1987). Synthetic analogues (indolactams) of (−)-indolactam-V are new congeners of the teleocidin class of tumor promoters. Jpn J Cancer Res 78, 577-582.

http://stemcells.nih.gov/info/scireport/2006report.htm (2006).

Jiang, W., Shi, Y., Zhao, D., Chen, S., Yong, J., Zhang, J., Qing, T., Sun, X., Zhang, P., Ding, M., et al. (2007). In vitro derivation of functional insulin-producing cells from human embryonic stem cells. Cell Res 17, 333-344.

Kambhampati, S., Li, Y., Verma, A., Sassano, A., Majchrzak, B., Deb, D. K., Parmar, S., Giafis, N., V., K. D., Rahman, A., et al. (2003). Activation of protein Kinase C by alltrans-retinoic acid. The Journal of biological chemistry 278, 32544-32551.

Kim, S. K., and Melton, D. A. (1998). Pancreas development is promoted by cyclopamine, a hedgehog signaling inhibitor. Proc Natl Acad Sci USA 95, 13036-13041.

Korsgren, O., Jansson, L., Eizirik, D., and Andersson, A. (1991). Functional and morphological differentiation of fetal porcine islet-like cell clusters after transplantation into nude mice. Diabetologia 34, 379-386.

Ku, H. T., Zhang, N., Kubo, A., O'Connor, R., Mao, M., Keller, G., and Bromberg, J. S. (2004). Committing embryonic stem cells to early endocrine pancreas in vitro. Stem Cells 22, 1205-1217.

Kubo, A., Shinozaki, K., Shannon, J. M., Kouskoff, V., Kennedy, M., Woo, S., Fehling, H. J., and Keller, G. (2004). Development of definitive endoderm from embryonic stem cells in culture. Development 131, 1651-1662.

Lumelsky, N., Blondel, O., Laeng, P., Velasco, I., Ravin, R., and McKay, R. (2001). Differentiation of embryonic stem cells to insulin-secreting structures similar to pancreatic islets. Science 292, 1389-1394.

McLean, A. B., D'Amour, K. A., Jones, K. L., Krishnamoorthy, M., Kulik, M. J., Reynolds, D. M., Sheppard, A. M., Liu, H., Xu, Y., Baetge, E. E., and Dalton, S. (2007). Activin a efficiently specifies definitive endoderm from human embryonic stem cells only when phosphatidylinositol 3-kinase signaling is suppressed. Stem Cells 25, 29-38.

Micallef, S. J., Janes, M. E., Knezevic, K., Davis, R. P., Elefanty, A. G., and Stanley, E. G. (2005). Retinoic acid induces Pdx1-positive endoderm in differentiating mouse embryonic stem cells. Diabetes 54, 301-305.

Movassat, J., Beattie, G. M., Lopez, A. D., and Hayek, A. (2002). Exendin 4 up-regulates expression of PDX 1 and hastens differentiation and maturation of human fetal pancreatic cells. J Clin Endocrinol Metab 87, 4775-4781.

Nakagawa, M., Koyanagi, M., Tanabe, K., Takahashi, K., Ichisaka, T., Aoi, T., Okita, K., Mochiduki, Y., Takizawa, N., and Yamanaka, S. (2007). Generation of induced pluripotent stem cells without Myc from mouse and human fibroblasts. Nat Biotechnol.

Osafune, K., Caron, L., Borowiak, M., Martinez, R. J., FitzGerald, C. S., Sato, Y., Cowan, C. A., Chien, K. R., and Melton, D. A. (2008). Marked differences in differentiation propensity among human embryonic stein cell lines. Nat Biotechnol.

Park, I. H., Zhao, R., West, J. A., Yabuuchi, A., Huo, H., Ince, T. A., Lerou, P. H., Lensch, M. W., and Daley, G. Q. (2008). Reprogramming of human somatic cells to pluripotency with defined factors. Nature 451, 141-146.

Rajagopal, J., Anderson, W. J., Kume, S., Martinez, O. I., and Melton, D. A. (2003). Insulin staining of ES cell progeny from insulin uptake. Science 299, 363.

Roy, S., Qiao, T., Wolff, C., and Ingham, P. W. (2001). Hedgehog signaling pathway is essential for pancreas specification in the zebrafish embryo. Curr Biol 11, 1358-1363.

Soria, B. (2001). In-vitro differentiation of pancreatic beta-cells. Differentiation 68, 205-219.

Stafford, D., and Prince, V. E. (2002). Retinoic acid signaling is required for a critical early step in zebrafish pancreatic development. Curr Biol 12, 1215-1220. Stainier, D. Y. (2002). A glimpse into the molecular entrails of endoderm formation. Genes Dev 16, 893-907.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Tiso, N., Filippi, A., Pauls, S., Bortolussi, M., and Argenton, F. (2002). BMP signalling regulates anteroposterior endoderm patterning in zebrafish. Mech Dev 118, 29-37.

Ueda, Y., Hirai, S., Osada, S., Suzuki, A., Mizuno, K., and Ohno, S. (1996). Protein kinase C activates the MEK-ERK pathway in a manner independent of Ras and dependent on Raf. J Biol Chem 271, 23512-23519.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced Pluripotent Stem Cell Lines Derived from Human Somatic Cells. Science.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A method of producing pancreatic Pdx1-expressing cells comprising:
    a) exposing a population of human embryonic stem (hES) cells to an effective amount of at least one compound listed in Table 1 and a compound selected from the group consisting of FGF10, Wnt3α, Activin A, Activin B and KAAD-cyclopamine to differentiate the hES cells into definitive endoderm cells, and
    b) obtaining a population of definitive endoderm cells which has increased expression of Pdx1 compared to a population of hES cells which were not exposed to a compound listed in Table 1.

2. A method of producing Pdx1-expressing pancreatic precursors comprising:
    a) exposing a population of hES cells to an effective amount of at least one compound selected from the group consisting of FGF10, Wnt3α, Activin B and KAAD-cyclopamine to differentiate the hES cells into definitive endoderm cells, and b) exposing the population of definitive endoderm cells to an effective amount of at least one compound listed in Table 1 to increase the percentage of Pdx-1 expressing precursors.

3. The method of claim 2, in which the at least one compound is compound 1 in table 1.

4. The method of claim 3, further comprising differentiating the Pdx1-expressing pancreatic precursors into mature pancreatic cells.

\* \* \* \* \*